United States Patent [19]
Voross

[11] 3,935,459
[45] Jan. 27, 1976

[54] APPARATUS AND METHOD OF AUTOMATICALLY ZEROING AN EXHAUST EMISSION ANALYZER

[75] Inventor: Zoltan Voross, Elgin, Ill.

[73] Assignee: Sun Electric Corporation, Chicago, Ill.

[22] Filed: June 24, 1974

[21] Appl. No.: 482,444

[52] U.S. Cl. ............................ 250/343; 250/343
[51] Int. Cl.² ........................................ G01N 21/26
[58] Field of Search .................... 250/252, 340, 343

[56] References Cited
UNITED STATES PATENTS

| | | | |
|---|---|---|---|
| 3,805,074 | 4/1974 | McCormack | 250/343 |
| 3,832,549 | 8/1974 | Mangan et al. | 250/252 X |

Primary Examiner—Davis L. Willis
Attorney, Agent, or Firm—Molinare, Allegretti, Newitt & Witcoff

[57] ABSTRACT

The automatic output zeroing apparatus includes an energy storage device and a differential operational amplifier. The energy storage device, which is connected to one input of the differential operational amplifier, is charged to a voltage representing the free air voltage generated by the exhaust emission analyzer. The other input of the differential operational amplifier receives the pollution-indicating voltage generated by the exhaust emission analyzer. The differential operational amplifier produces a modified pollution-indicating voltage, representing the difference between the generated pollution-indicating voltage and the free air voltage.

18 Claims, 2 Drawing Figures

APPARATUS AND METHOD OF AUTOMATICALLY ZEROING AN EXHAUST EMISSION ANALYZER

BACKGROUND OF THE INVENTION

The present invention relates generally to an apparatus and method for automatically zeroing an output and, more particularly, to an automatic output zero for an exhaust emission analyzer and a method of use.

The presently known exhaust emission analyzers include a probe which is inserted into the exhaust pipe of the automobile to be tested. Once the probe is inserted, the pollution analyzer generates a pollution-indicating voltage which produces an output meter deflection, indicating the level of pollution in the exhausted air.

In many instances, the generated pollution-indicating voltage is inaccurate. For various reasons, such as the accumulation of dirt and dust particles in the optical path and aging of the infrared source of the analyzer, the generated pollution-indicating voltage can include a "free air" component, representing the voltage generated by the analyzer during analysis of open environmental air, i.e., with the probe exposed to clean atmospheric air. As such, the generated pollution-indicating voltage represents the sum of the true pollution-indicating voltage and free air voltage. The result is an erroneous pollution level indication.

The presently known analyzers include a potentiometer which is adjusted by the operator to zero the output meter just prior to the pollution test. The requirement of a manual adjustment, however, directly introduces human error into the compensating or zeroing process. Clearly, if the meter is not properly adjusted, the indicated pollution level remains inaccurate.

SUMMARY OF THE INVENTION

In a principal aspect, the present invention comprises an automatic output zeroing apparatus and method of use wherein the generated pollution-indicating voltage is modified to suppress the effect of the free air voltage component. The modified pollution-indicating voltage represents the difference between the generated pollution-indicating voltage and the free air voltage.

More particularly, the automatic output zero includes means for retrievably storing or memorizing the free air voltage and means for summing the generated pollution-indicating voltage and free air voltage to produce the modified pollution-indicating voltage. Switch means, operable in at least two states, connect the storing or memorizing means to the input during free air analysis, i.e., generation of the free air voltage alone, and disconnect the storing means therefrom during analysis of exhausted air.

In utilizing the automatic output zero described above, the operator of the exhaust emission analyzer initially exposes the probe to the open environment, thereby generating the free air voltage and charging the storing means. After disconnecting the storing means from the exhaust emission analyzer, the operator then inserts the probe in the exhaust pipe of the automobile to be tested. The pollution-indicating voltage, thus generated, is opposed by the stored free air voltage to produce a modified and substantially more accurate pollution-indicating voltage.

It is thus an object of the present invention to provide an automatic output zero for an exhaust emission analyzer and a method of use therefor.

It is a further object of the present invention to provide an automatic output zero and method of use whereby the effect of the free air voltage generated by the exhaust emission analyzer is substantially suppressed and minimized.

It is also an object of the present invention to provide an automatic output zero and method of use wherein the generated pollution-indicating voltage is opposed by the free air voltage to produce a modified, or corrected, pollution-indicating voltage.

These and other objects and advantages of the present invention will become apparent in the following detailed description.

BRIEF DESCRIPTION OF THE DRAWING

The present invention will be described, in detail, with reference to the drawing wherein.

DETAILED DESCRIPTION OF THE PRESENT INVENTION

Figure 1:
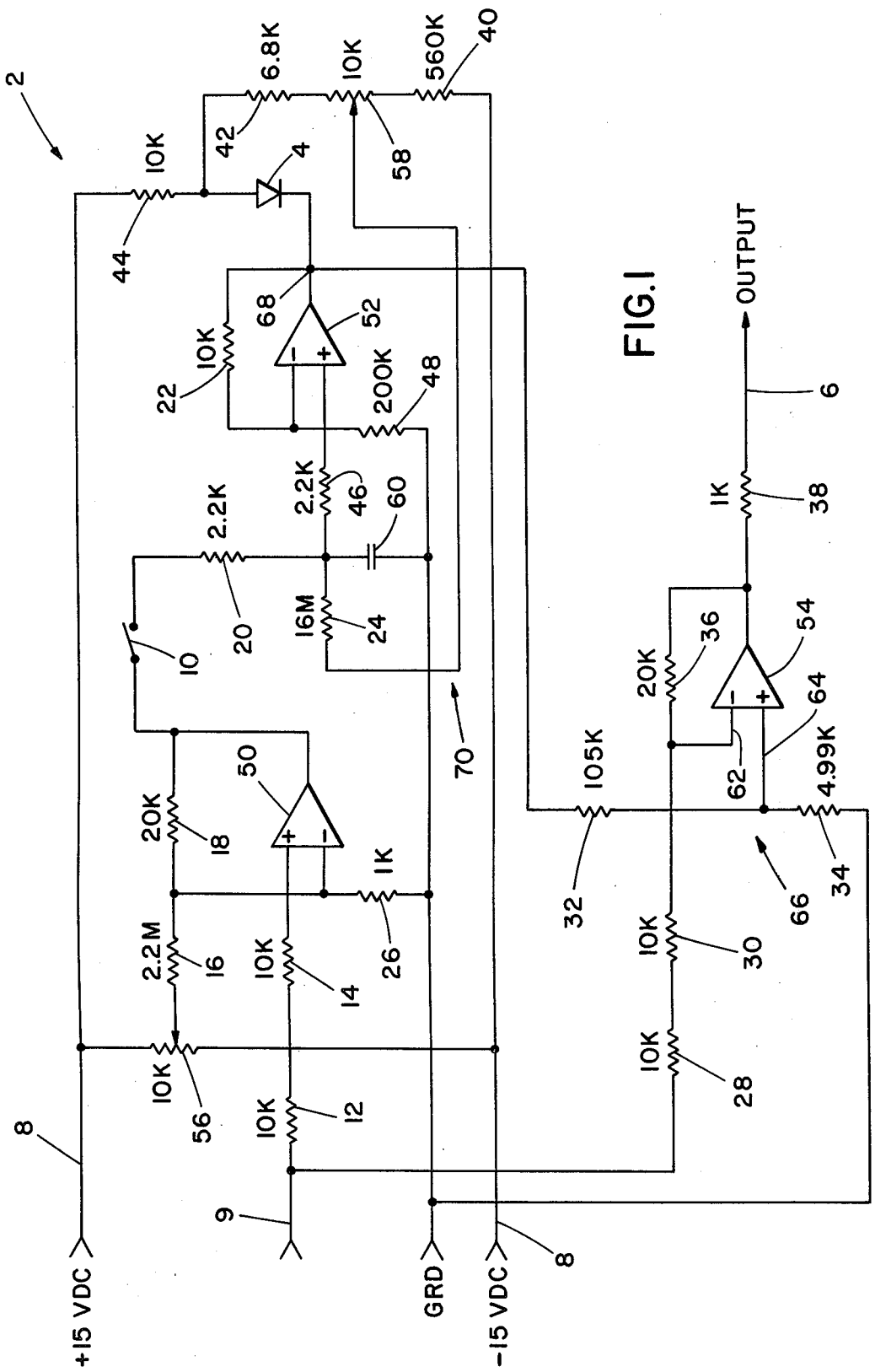
FIG. 1 is a circuit diagram showing a preferred embodiment of the present invention.

A preferred embodiment of the present invention is shown in FIG. 1 and generally designated as an automatic output zeroing apparatus 2. The circuitry of the automatic output zero 2 includes a diode 4, an output 6, a pair of biasing voltage sources 8, a zeroing switch 10, resistors 12–48, amplifiers 50–54, potentiometers 56–58, and a memory capacitor 60, connected as shown.

Figure 2:
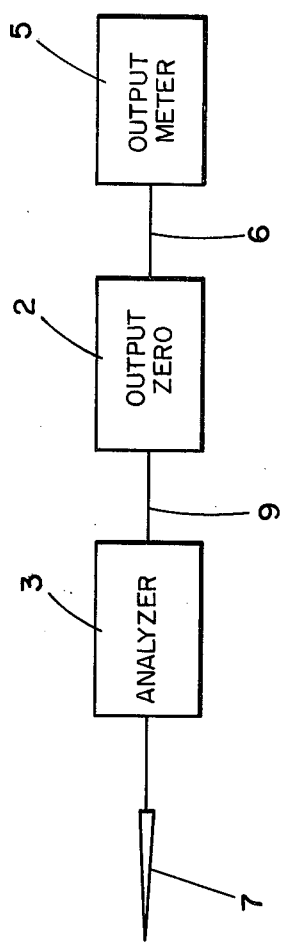
FIG. 2 is a schematic diagram showing an exhaust emission analyzer including the preferred embodiment of the present invention shown in FIG. 1.
Figure 2:
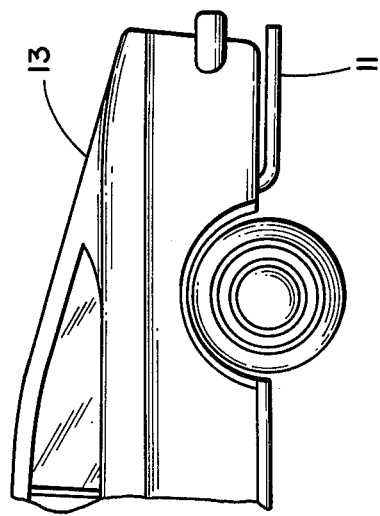

As shown in FIG. 2, the automatic output zero 2 is interconnected between an exhaust emission analyzer 3 and an output meter 5, and the apparatus 2 is used to zero the reading on the output meter 5. The apparatus 2, however, could be readily used in conjunction with the other output devices, such as a computer, printer, or multiplexer.

The exhaust emission analyzer 3 is representative of the "Exhaust Performance Analyzers" presently produced and manufactured by the Sun Electric Corporation of Chicago, Ill. The analyzer 3 includes a probe 7 and an output 9. With the probe 7 inserted in the exhaust pipe 11 of an automobile 13, the analyzer 3 generates a pollution-indicating voltage.

As previously discussed, the generated pollution-indicating voltage includes an error component representing the free air voltage generated by the analyzer. To substantially suppress and minimize the effect of the free air voltage, it is necessary to initially determine and store, or memorize, the magnitude of this free air voltage.

To accomplish determination and storage, the operator (not shown) of the exhaust emission analyzer 3 closes the zeroing switch 10 and exposes the probe 7 to the environment. The zeroing switch 10 is closed by depression of a button (not shown) on the exhaust emission analyzer 3. The zeroing switch 10 is spring biased to a normally open state.

Closing of the zeroing switch 10 connects the memory capacitor 60 to the output 9 through the operational amplifier 50. As such, the memory capacitor 60 is charged to a voltage proportional to the free air voltage. The proportionality constant is the gain factor of the amplifier 50.

In the preferred embodiment shown, the gain factor of the amplifier 50 is 21. The free air voltage is amplified prior to storage to substantially avoid a significant percentage drop in the voltage across the memory capacitor 60 due to various leakages in the circuitry. That is, for a given amount of current leakage, the percent drop in the memory capacitor 60 voltage, due to leakage, is substantially reduced by amplification prior to storage.

Having stored the free air voltage, the operator opens the zeroing switch 10, disconnecting the memory capacitor 60 from the output 9, and inserts the probe 7 into the exhaust pipe 11 of the automobile 13 being tested. The generated pollution-indicating voltage is now received by an input terminal 62 of the summing amplifier 54, a differential operational amplifier.

The other input terminal 64 of the summing amplifier 54 is connected to the memory capacitor 60 through a voltage divider, generally designated 66, comprising resistors 32, 34, and the high impedance operational amplifier 52. The operational amplifier 52 has an output 68. The gain factor of the amplifier 52 is this preferred embodiment of the automatic meter zero 2 is 1.05. The significance of the amplifier 52 is discussed in detail below.

The voltage divider 66 effectively cancels the two previous amplifications of the free air signal. That is, the voltage at the input terminal 64 of the summing amplifier 54 is substantially equal to the free air voltage generated by the exhaust emission analyzer 3.

The output of the summing amplifier 54 is a modified pollution-indicating voltage representing the difference between the generated pollution-indicating voltage and the free air voltage. Thus, by opposing the generated pollution-indicating voltage with the stored free air voltage, the adverse effect of the free air voltage is substantially avoided.

After each pollution test, the operator again closes the zeroing switch 10 to "update" the voltage on the memory capacitor 60. The magnitude of the free air voltage, however, will not vary significantly over a short period of time, e.g., several hours, and thus, the "updating" procedure need not be meticulously followed.

A significant function of the operational amplifier 52 is to transfer the free air voltage to the voltage divider 66 and the summing amplifier 54, without unduly loading the memory capacitor 60. Additionally, the amplifier 52, in cooperation with the potentiometer 58 and diode 4, charges, or more appropriately recharges, the memory capacitor 60 to compensate for current leakage.

Leakage occurs in the memory capacitor 60 itself, the amplifier 52, and the printed circuit board (not shown). The leakage includes two components, i.e., a voltage variable component dependent on the memory capacitor 60 voltage and a temperature variable component dependent upon the temperature sensitivity of the operational amplifier 52.

Basically, the greater-than-one gain of the amplifier 52 compensates for the voltage variable leakage. As shown, the output 68 of the amplifier 52 is connected through a feedback loop 70 to the memory capacitor 60, thereby recharging the memory capacitor 60 through the resistor 24.

The amount of voltage variable feedback current is regulated by the potentiometer 58. The potentiometer 58 is adjusted with the memory capacitor 60 charged to a predetermined voltage and the zeroing switch 10 open. Adjustment is made until the voltage at the output 68 remains constant. At that point, the recharging current is substantially equal to the current leakage or draw on the memory capacitor 60.

The adjustment of the potentiometer 58 is a once-a-lifetime adjustment. However, readjustment will be necessary whenever parts of the automatic meter zero 2 are repaired or replaced.

With the potentiometer 58 set, a voltage variable feedback current is established. The diode 4 regulates this feedback current as a function of temperature to compensate for the temperature sensitivity of the amplifier 52. That is, a decrease in temperature will increase the leakage current through the amplifier 52. The feedback current, however, will also increase due to the temperature sensitivity of the diode 4, and thus, the memory capacitor 60 voltage is maintained at a substantially constant level during a pollution test.

The feedback circuitry is a significant feature of the automatic meter zero 2 because it permits the use of inexpensive operational amplifiers. As indicated, the feedback circuitry maintains the voltage across the memory capacitor 60, despite amplifier leakage, and expensive, non-leaking amplifiers are, therefore, unnecessary.

The potentiometer 56 provides a constant current feed to compensate for the total offset of the three operational amplifiers 50, 52, 54. The potentiometer 56 is also adjusted only once during the lifetime of the automatic meter zero 2. The adjustment is accomplished with the output 9 shorted and the zeroing switch 10 closed. Adjustment is made until the deflection of the output meter is zero.

A single preferred embodiment of the present invention has been shown and described in detail. It is to be understood, however, that various changes and modifications of the automatic meter zero 2 can be made without departing from the true spirit and scope of the present invention, as defined by the following claims.

What is claimed is:

1. An automatic output zeroing apparatus for an exhaust emission analyzer having output means, said exhaust emission analyzer generating a free air voltage during analysis of open environmental air and a pollution-indicating voltage during analysis of air exhausted from an automobile, comprising, in combination:

means for retrievably storing a first voltage proportional to said free air voltage;

switch means operable in a first state for connecting said storing means to said exhaust emission analyzer and operable in at least a second state for disconnecting said storing means from said exhaust emission analyzer, said switch means being operated in said first state during analysis of said open environmental air and in said second state during analysis of said exhausted air; and means for summing a second voltage proportional to said pollution-indicating voltage and said first voltage to produce an output signal, said output means being responsive to said output signal, said output signal representing the difference between said second voltage and said first voltage, said summing means being responsive to said exhaust emission analyzer and said storing means.

2. An automatic output zero as claimed in claim 1 wherein said summing means includes a differential operational amplifier.

3. An automatic output zero as claimed in claim 1 wherein said storing means includes an energy storage device.

4. An automatic output zero as claimed in claim 3 wherein said energy storage device is a capacitor.

5. An automatic output zero as claimed in claim 3 further comprising means for charging said energy storage device with a feedback current to substantially counterbalance the load on said energy storage device, whereby the voltage across said energy storage device remains substantially equivalent to said free air voltage.

6. An automatic output zero as claimed in claim 5 wherein said charging means includes means for amplifying said stored free air voltage, said amplifying means having an output, and means for connecting said output and said energy storage device.

7. An automatic output zero as claimed in claim 5 wherein said charging means includes means for regulating said feedback current as a function of temperature.

8. An automatic output zero as claimed in claim 7 wherein said temperature-sensitive regulating means includes a diode.

9. An automatic output zero as claimed in claim 5 wherein said charging means includes variable resistance means for regulating said feedback current.

10. An automatic output zero as claimed in claim 1 further comprising means for amplifying said free air voltage to produce said first voltage.

11. An automatic output zero as claimed in claim 10 wherein said summing means includes means for attenuating said first voltage prior to summation.

12. An automatic output zero as claimed in claim 11 wherein said attenuating means is a voltage divider.

13. In an exhaust emission analyzer having an output means, said exhaust emission analyzer being of the type which generates a pollution-indicating voltage during analysis of air exhausted from an automobile, said pollution-indicating voltage including an error component representing the free air voltage generated by said exhaust emission analyzer during analysis of open environmental air, the improvement comprising, in combination:
means for memorizing the magnitude of said free air voltage;
switch means operable in a first state during analysis of said open environmental air for connecting said memorizing means to said exhaust emission analyzer and operable in at least a second state during analysis of said exhausted air for disconnecting said memorizing means from said exhaust emission analyzer; and
summing means for producing a modified pollution-indicating voltage, said summing means being responsive to said exhaust emission analyzer and said memorizing means, said modified pollution-indicating voltage being proportional to the difference between said pollution-indicating voltage and said free air voltage, said output means being responsive to said summing means.

14. An improvement as claimed in claim 13 wherein said memorizing means includes a capacitor, said capacitor being charged to a voltage substantially proportional to said free air voltage during first state operation of said switch means.

15. An improvement as claimed in claim 14 further comprising means for charging said capacitor during second state operation of said switch means to compensate for current drawn from said capacitor, whereby said capacitor voltage remains substantially equal to said free air voltage.

16. A method for automatically zeroing an exhaust emission analyzer for an automobile having an exhaust pipe, said analyzer having a probe, voltage generating means, output means, and storing means, comprising the steps of:
interconnecting said storing means and said voltage generating means;
exposing said probe to the free environmental air, whereby said analyzer generates a free air voltage;
continuing to interconnect said storing means and said voltage generating means until said storing means is charged to a first voltage proportional to said free air voltage;
disconnecting said storing means and said voltage generating means;
inserting said probe in said exhaust pipe, whereby said analyzer generates a pollution-indicating voltage; and
opposing said pollution-indicating voltage and said first voltage to produce a modified pollution-indicating voltage, said output means responding to said modified pollution-indicating voltage.

17. A method as claimed in claim 16 wherin said opposing step includes summing said pollution-indicating voltage and said first voltage, said modified pollution-indicating voltage being proportional to the difference between said pollution-indicating voltage and said first voltage.

18. A method as claimed in claim 16 further comprising the step of recharging said storing means, whereby said first voltage remains substantially constant during operation of said analyzer.

* * * * *